US00PP28777P3

(12) United States Plant Patent
Commeraat

(10) Patent No.: US PP28,777 P3
(45) Date of Patent: Dec. 19, 2017

(54) ***VERONICA* PLANT NAMED 'JOCA128'**

(50) Latin Name: *Veronica spicata*
Varietal Denomination: Joca128

(71) Applicant: Johannes Gerardus Commeraat, Boskoop (NL)

(72) Inventor: Johannes Gerardus Commeraat, Boskoop (NL)

( * ) Notice: Subject to any disclaimer, the term of this patent is extended or adjusted under 35 U.S.C. 154(b) by 80 days.

(21) Appl. No.: 14/998,782

(22) Filed: Feb. 16, 2016

(65) Prior Publication Data

US 2017/0118898 P1 Apr. 27, 2017

(30) Foreign Application Priority Data

Oct. 26, 2015 (QZ) ..... PBR 2015/2453

(51) Int. Cl.
*A01H 5/02* (2006.01)

(52) U.S. Cl.
USPC ..... Plt./251

(58) Field of Classification Search
USPC ..... Plt./251
See application file for complete search history.

(56) References Cited

PUBLICATIONS

UPOV hit on *Veronica* plant named 'Joca128', QZ PBR 20152453, published Dec. 15, 2015.*

* cited by examiner

*Primary Examiner* — Anne Grunberg
(74) *Attorney, Agent, or Firm* — Penny J. Aguirre

(57) ABSTRACT

A new cultivar of *Veronica* plant, 'Joca128', that is characterized by its dwarf plant habit, its large inflorescences of white flowers, and its floriferous blooming habit with numerous flowering stems and numerous flowers per flowering stem.

2 Drawing Sheets

Botanical classification: *Veronica spicata.*
Variety denomination: 'Joca128'.

BACKGROUND OF THE INVENTION

The present invention relates to a new and distinct cultivar of *Veronica spicata* and will be referred to hereafter by its cultivar name, 'Joca128'. 'Joca128' represents a new herbaceous perennial grown for landscape use.

'Joca128' arose from seed collected in autumn of 2009 from an open pollinated plant of *Veronica spicata* 'Ulster Blue Dwarf' (not patented) as the female seed parent. The seeds was sown in 2010 and 'Joca128' was selected in autumn of 2011 as a single unique plant amongst the resulting seedlings.

Asexual propagation of the new cultivar was first accomplished by softwood cuttings by the Inventor in winter of 2011 in Boskoop, The Netherlands. Asexual propagation by vegetative cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Joca128' as a unique cultivar of *Veronica.*

1. 'Joca128' exhibits a dwarf plant habit.
2. 'Joca128' exhibits large inflorescences of white flowers.

3. 'Joca128' exhibits a floriferous blooming habit with numerous flowering stems and numerous flowers per flowering stem.

The parent plant of 'Joca128', 'Ulster Blue Dwarf', differs from 'Joca128' in having flowers that are blue in color. 'Joca128' can be most closely compared to the *Veronica spicata* cultivars 'Verswhite' (U.S. Plant Pat. No. 24,784) and 'Icicle' (not patented). 'Verswhite' is similar to 'Joca128' in having an upright dwarf plant habit and having flowers that are white in color. 'Verswhite' differs from 'Joca128' in having smaller leaves and in having fewer flowers per flowering stem. 'Icicle' is similar to 'Joca128' in having white colored flowers, but differs most significantly from 'Joca128' in having a larger, non-dwarf plant habit.

BRIEF DESCRIPTION OF THE DRAWINGS

The accompanying colored photographs illustrate the overall appearance and distinct characteristics of the new *Veronica.* The photographs were taken of a one year-old plant of 'Joca128' as field grown in Haarlem, The Netherlands.

The photograph in FIG. 1 provides a side view of a plant of 'Joca128' in bloom.

Figure 1:
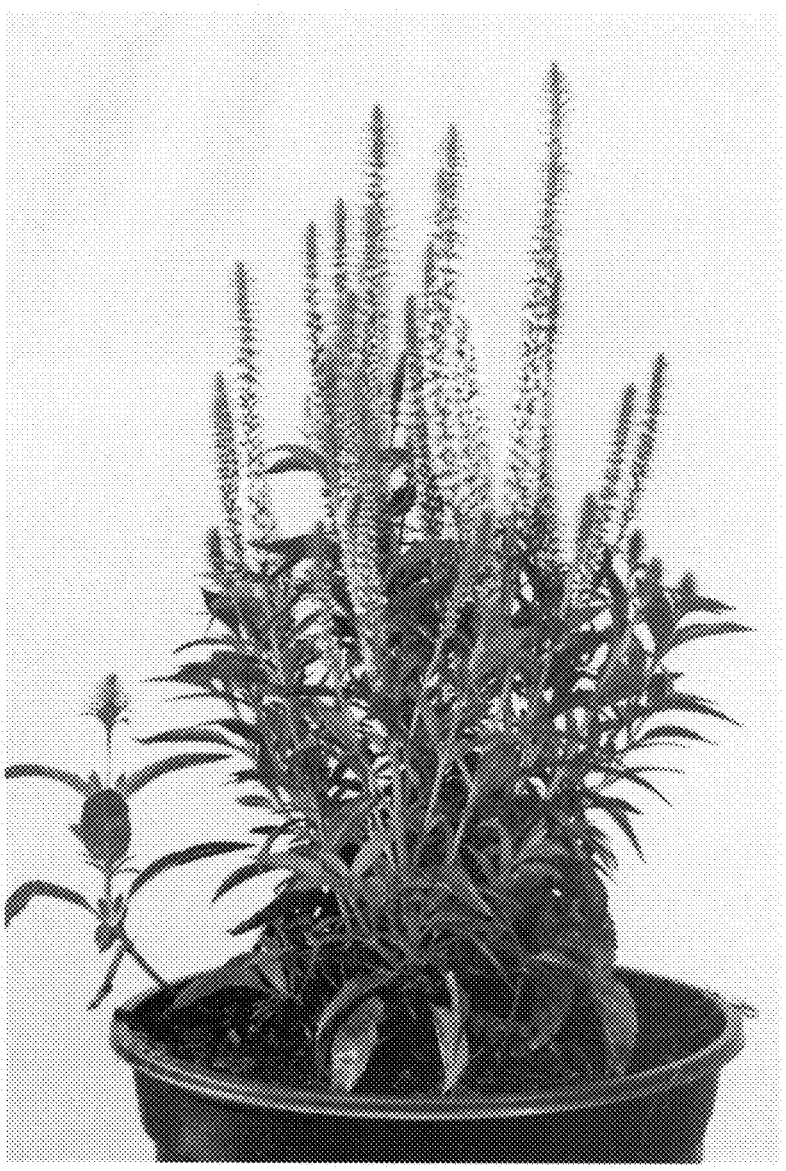
Figure 2:
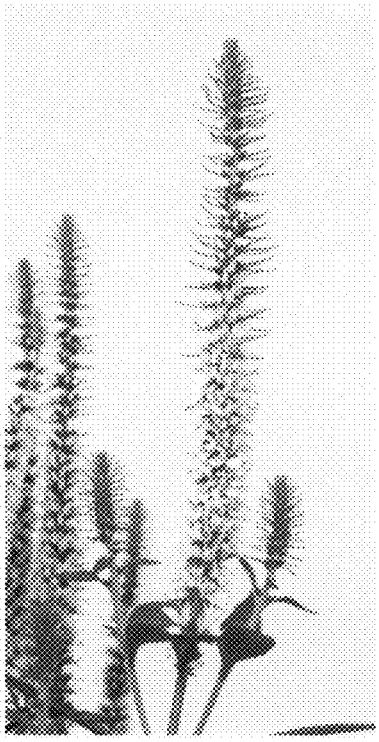

The photograph in FIG. 2 provides a close-up view of an inflorescence of 'Joca128'.

Figure 3:
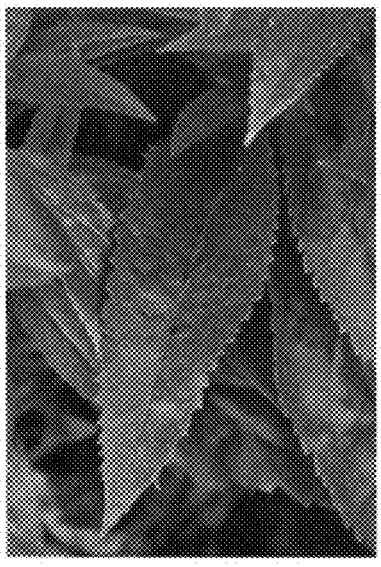

The photograph in FIG. 3 provides a close-up view of the foliage of 'Joca128'.

The colors in the photographs may differ slightly from the color values cited in the detailed botanical description, which accurately describe the colors of the new *Veronica.*

DETAILED BOTANICAL DESCRIPTION

The following is a detailed description of the new cultivar as observed for a plant about one year in age as grown outdoors in 19-cm containers in Haarlem, The Netherlands. The plants were grown under average day temperatures of 16° to 30° C. and average night temperatures of 5° to 20° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—From mid-summer to autumn.

*Plant type.*—Herbaceous perennial.

*Plant habit.*—Broad upright.

*Height and spread.*—Reaches 28.9 cm in height and 24 cm in spread.

*Hardiness.*—At least hardy in U.S.D.A. Zone 4.

*Diseases.*—Not more susceptible to pests and diseases than other *Veronica* varieties.

*Root description.*—Fibrous and fine.

*Propagation.*—Stem cuttings.

*Root development.*—About 2 weeks to initiate roots from a cutting and about 6 weeks to finish a young plant.

*Growth rate.*—Moderate.

Stem description:

*Shape.*—Round.

*Stem quantity.*—Average of 11 main stems each with an average of 2 lateral branches.

*Stem color.*—144A.

*Stem size.*—Average of 2 cm in diameter and 10.5 cm (excluding peduncle) in length, internode is 2.3 cm in length.

*Stem surface.*—Glossy.

*Stem strength.*—Strong.

*Stem aspect.*—Held at an average angle of 30° to main stem.

*Branching habit.*—Free branching from the base with lateral branches.

Foliage description:

*Leaf division.*—Simple.

*Leaf arrangement.*—Opposite.

*Leaf shape.*—Narrow ovate and slightly carinate.

*Leaf size.*—An average of 4.5 cm in length and 1.6 cm in width.

*Leaf number.*—Average of 10 per branch.

*Leaf base.*—Obtuse.

*Leaf apex.*—Acute.

*Leaf margin.*—Finely serrate with an average of 4.5 teeth per cm.

*Leaf venation.*—Pinnate, upper surface 146D in color, lower surface 138B in color.

*Leaf surface texture.*—Upper surface moderately glossy, lower surface slightly glossy.

*Leaf color.*—Young upper surface; 143A to 143B, young lower surface; 138A to 138B, mature upper surface; N137A to N137B, mature lower surface; between 137C and 147B.

*Petiole.*—Carinate in shape, average of 7 mm in length and an average of 2.5 mm in width and 2 mm in height, upper side color is 144A, lower side color is 144B, surface texture glabrous.

Flower description:

*Inflorescence type.*—Terminal and axillary racemes of rotate-shaped flowers.

*Lastingness of inflorescence.*—Individual flowers up to 7 days, blooms open from bottom of raceme towards apex.

*Inflorescence size.*—Average of 12.3 cm in length and 1.6 cm in diameter.

*Flower type.*—Outward and campanulate in shape.

*Flower number.*—Average of 240 per compound inflorescence, average of 5,000 flowers and buds per plant.

*Flower fragrance.*—None.

*Flower buds.*—Ovate in shape, about 2.5 mm in length and 1 mm in diameter, color is NN155D.

*Flower size.*—About 4 mm in depth and 5 mm in diameter.

*Peduncles.*—11.9 cm in length, 1.8 mm in diameter, held straight on top of stems, strong, 143B in color, surface texture is glabrous.

*Pedicels.*—None, individual flowers sessile.

*Calyx.*—Rotate in shape, an average of 2 mm in length and 2.5 mm in diameter.

*Sepals.*—4, rotate, narrow ovate in shape, base is obtuse, matte and glabrous surfaces, entire margins sparsely covered with pubescence average of 0.3 mm in length and too small to measure color, acute apex, average of 2 mm in length and 0.8 mm in width, color of immature and mature upper and lower surfaces; 137B.

*Petals.*—4, campanulate in shape, acute apex, lower 25% fused, mostly entire margin with one tooth on each side, average of 4 mm in length and 1 mm in width, both surfaces matte and glabrous, color of upper side and lower side when opening and fully open; NN155D, veined and marbled with 94C.

Reproductive organs:

*Gynoecium.*—Pistil; 1, 6 mm in length, stigma; clavate in shape, 157D in color, style; 5.5 mm in length, NN155D in color, ovary; 144A in color.

*Androecium.*—Stamens; 2, deformed in shape, anthers; no anthers present, only deformed filaments, filaments; 2.5 mm in length, 145B in color, tinged N186B in color, no pollen present.

*Fruit.*—Fruit and seed production was not observed.

It is claimed:

1. A new and distinct cultivar of *Veronica* plant named 'Joca128' as herein illustrated and described.

* * * * *